US012357379B2

(12) United States Patent
Nguyen et al.

(10) Patent No.: US 12,357,379 B2
(45) Date of Patent: *Jul. 15, 2025

(54) PULMONARY VEIN ISOLATION BALLOON CATHETER

(71) Applicant: St. Jude Medical, Cardiology Division, Inc., St. Paul, MN (US)

(72) Inventors: Tho Nguyen, Huntington Beach, CA (US); Tim La, Santa Ana, CA (US); Alan de la Rama, Cerritos, CA (US); Cary Hata, Irvine, CA (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 82 days.

This patent is subject to a terminal disclaimer.

(21) Appl. No.: 18/217,234

(22) Filed: Jun. 30, 2023

(65) Prior Publication Data

US 2024/0081899 A1 Mar. 14, 2024

Related U.S. Application Data

(63) Continuation of application No. 16/475,676, filed as application No. PCT/US2018/012308 on Jan. 4, 2018, now Pat. No. 11,737,820.

(60) Provisional application No. 62/443,228, filed on Jan. 6, 2017.

(51) Int. Cl.
*A61B 18/12* (2006.01)
*A61B 18/14* (2006.01)
*A61L 29/08* (2006.01)
*A61B 18/00* (2006.01)
(Continued)

(52) U.S. Cl.
CPC ........ *A61B 18/1492* (2013.01); *A61L 29/085* (2013.01); *A61B 2018/00107* (2013.01); *A61B 2018/0022* (2013.01); *A61B 2018/00351* (2013.01); *A61B 2018/00404* (2013.01); *A61B 2018/00541* (2013.01); *A61B 2018/00577* (2013.01); *A61B 2018/00839* (2013.01);
(Continued)

(58) Field of Classification Search
CPC ................ A61B 18/02; A61B 18/1492; A61B 2018/00107; A61B 2018/0022; A61B 2018/00351; A61B 2018/00404; A61B 2018/00541; A61B 2018/00577; A61B 2018/00839; A61B 2018/0212; A61B 2018/1472
See application file for complete search history.

(56) References Cited

U.S. PATENT DOCUMENTS

| 6,291,568 B1 | 9/2001 | Lussey |
| 6,416,511 B1 | 7/2002 | Lesh et al. |
| 6,495,069 B1 | 12/2002 | Lussey et al. |

(Continued)

FOREIGN PATENT DOCUMENTS

| WO | 0056237 A1 | 9/2000 |
| WO | 0187174 A1 | 11/2001 |

(Continued)

*Primary Examiner* — Daniel W Fowler
(74) *Attorney, Agent, or Firm* — Armstrong Teasdale LLP

(57) ABSTRACT

The instant disclosure relates to electrophysiology catheters for tissue ablation within a cardiac muscle, for example. In particular, the instant disclosure relates to an electrophysiology ablation balloon catheter with a combination of coated and uncoated surfaces for focusing ablation energy at a desired portion of tissue.

18 Claims, 8 Drawing Sheets

(51) Int. Cl.
*A61B 18/02* (2006.01)
*A61B 90/00* (2016.01)

(52) U.S. Cl.
CPC ............. *A61B 2018/0212* (2013.01); *A61B 2090/0481* (2016.02)

(56) References Cited

U.S. PATENT DOCUMENTS

| | | |
|---|---|---|
| 6,514,249 B1 | 2/2003 | Maguire et al. |
| 6,646,540 B1 | 11/2003 | Lussey |
| 6,952,615 B2 | 10/2005 | Satake |
| 6,999,821 B2 | 2/2006 | Jenney et al. |
| 7,112,198 B2 | 9/2006 | Satake |
| 7,736,362 B2 | 6/2010 | Eberl et al. |
| 7,955,326 B2 | 6/2011 | Paul et al. |
| 8,231,617 B2 | 7/2012 | Satake |
| 8,500,730 B2 | 8/2013 | Lee et al. |
| 8,647,339 B2 | 2/2014 | Satake |
| 2004/0260277 A1 | 12/2004 | Maguire |
| 2005/0070887 A1 | 3/2005 | Taimisto et al. |
| 2005/0203597 A1 | 9/2005 | Yamazaki et al. |
| 2006/0069385 A1 | 3/2006 | Lafontaine et al. |
| 2009/0157066 A1 | 6/2009 | Satake |
| 2009/0299355 A1 | 12/2009 | Bencini et al. |
| 2010/0100087 A1* | 4/2010 | Mazzone .............. A61B 18/02 29/428 |
| 2010/0204560 A1 | 8/2010 | Salahieh et al. |
| 2012/0053577 A1 | 3/2012 | Lee et al. |
| 2012/0130363 A1 | 5/2012 | Isaac et al. |
| 2013/0030425 A1 | 1/2013 | Stewart et al. |
| 2013/0172877 A1 | 7/2013 | Subramaniam et al. |
| 2013/0197497 A1 | 8/2013 | Wittenerger et al. |
| 2014/0378966 A1 | 12/2014 | Haverkost et al. |
| 2014/0378967 A1* | 12/2014 | Willard .............. A61B 18/1492 606/41 |
| 2015/0141982 A1 | 5/2015 | Lee |
| 2017/0354463 A1 | 12/2017 | Mori |
| 2018/0360531 A1 | 12/2018 | Holmes et al. |

FOREIGN PATENT DOCUMENTS

| | | |
|---|---|---|
| WO | 2009137819 A1 | 11/2009 |
| WO | 2011143468 A2 | 11/2011 |
| WO | 2013040297 A1 | 3/2013 |
| WO | 2016210437 A1 | 12/2016 |

* cited by examiner

PULMONARY VEIN ISOLATION BALLOON CATHETER

CROSS-REFERENCE TO RELATED APPLICATIONS

This application claims the benefit of U.S. Provisional Application No. 62/443,228, filed 6 Jan. 2017, the entire disclosure of which is hereby incorporated by reference as though fully set forth herein.

BACKGROUND a. Field

The instant disclosure relates to catheters, in particular catheters for conducting ablation therapy within a heart or other tissue. In one embodiment, the instant disclosure relates to a catheter for treating cardiac arrhythmias by ablating in the vicinity of pulmonary venous tissue.

b. Background Art

The human heart routinely experiences electrical currents traversing its many surfaces and ventricles, including the endocardial chamber. Just prior to each heart contraction, the heart depolarizes and repolarizes, as electrical currents spread across the heart and throughout the body. In healthy hearts, the surfaces and ventricles of the heart will experience an orderly progression of depolarization waves. In unhealthy hearts, such as those experiencing atrial arrhythmia, including for example, ectopic atrial tachycardia, atrial fibrillation, and atrial flutter, the progression of the depolarization wave becomes chaotic. Arrhythmias may persist as a result of scar tissue or other obstacles to rapid and uniform depolarization. These obstacles may cause depolarization waves to electrically circulate through some parts of the heart more than once. Atrial arrhythmia can create a variety of dangerous conditions, including irregular heart rates, loss of synchronous atrioventricular contractions, and blood flow stasis. All of these conditions have been associated with a variety of ailments, and death.

Intravascular catheters are used in a variety of diagnostic and/or therapeutic medical procedures to correct conditions such as atrial arrhythmia, including for example, ectopic atrial tachycardia, atrial fibrillation, and atrial flutter.

Typically in an atrial fibrillation therapy, a catheter is manipulated through a patient's vasculature and into a patient's heart. The catheter may carry one or more electrodes which may be used for mapping, ablation, diagnosis, or other treatments. To alleviate symptoms related to atrial fibrillation, a distal end of the catheter imparts ablative energy to cardiac tissue to create a lesion in the cardiac tissue. The lesioned tissue is less capable of conducting electrical signals, thereby disrupting undesirable electrical pathways and limiting or preventing stray electrical signals that lead to arrhythmias. The ablation catheter may utilize ablative energy including, for example, radio frequency (RF), cryoablation, laser, chemical, and high-intensity focused ultrasound.

The foregoing discussion is intended only to illustrate the present field and should not be taken as a disavowal of claim scope.

BRIEF SUMMARY

The instant disclosure relates to electrophysiology catheters for tissue ablation within the heart or other tissue. In particular, the instant disclosure relates to an electrophysiology ablation balloon catheter with a combination of coated and uncoated surfaces for focusing ablative energy at a desired portion of tissue.

Aspects of the present disclosure are directed to an ablation balloon catheter including a catheter shaft, an ablation balloon with proximal and distal ends, and a radio frequency coil within the ablation balloon. The proximal end of the ablation balloon is coupled to a distal portion of the catheter shaft. The ablation balloon further includes an uncoated region that facilitates energy transfer between the ablation balloon and tissue in contact with the uncoated region, and a coated region that mitigates energy transfer between the ablation balloon and tissue in contact with the coated region. The radio frequency coil within the ablation balloon transmits radio frequency waves through the uncoated region of the ablation balloon to ablate tissue in contact with the uncoated region. In more specific embodiments, the uncoated region of the ablation balloon engages a pulmonary vein, and ablates tissue along a circumferential region around the pulmonary vein.

Some embodiments are directed to systems for treating atrial fibrillation. The system may include an introducer including a lumen extending through the introducer, a balloon delivery catheter with an ablation balloon coupled to a distal end, and a plurality of diagnostic electrodes. To conduct the atrial fibrillation treatment, the balloon delivery catheter is extended through the lumen of the introducer. The ablation balloon, which includes coated and uncoated regions, engages with a tissue wall of a pulmonary vein along the uncoated region of the ablation balloon. The ablation balloon delivers an ablation therapy along the tissue wall of the pulmonary vein engaged by the uncoated region of the balloon. The plurality of diagnostic electrodes are circumferentially distributed about the ablation balloon near a border between the coated and uncoated regions. In some specific implementations, the coated region of the ablation balloon insulates the tissue wall and the blood pool of the pulmonary vein engaged with the coated region from the ablation therapy.

Yet other embodiments are directed to a balloon catheter for pulmonary vein isolation. The balloon catheter includes a steerable balloon delivery catheter shaft, an ablation balloon coupled to a distal end of the steerable balloon delivery catheter shaft, and a tissue ablation means. The steerable balloon delivery catheter shaft deploys the ablation balloon into a pulmonary vein. The ablation balloon includes a combination of coated and uncoated regions on an outer surface of the ablation balloon. The coated and uncoated regions form an undulating border around a circumference of the ablation balloon. The ablation balloon deploys from an undeployed configuration, and engages a tissue wall of the pulmonary vein along the uncoated region of the ablation balloon. The tissue ablation means, in conjunction with the ablation balloon, delivers an ablation therapy to the tissue wall of the pulmonary vein in contact with the uncoated region of the ablation balloon. In some specific embodiments, the uncoated region is at a distal end of the ablation balloon, and the coated region is proximal the distal uncoated region. The uncoated region engages an antral circumference of the pulmonary vein and conducts tissue ablation therapy of the antral circumference of the pulmonary vein tissue in contact with the uncoated region. The coated region insulates a blood pool and pulmonary vein tissue in contact with the coated region from the ablation therapy.

The foregoing and other aspects, features, details, utilities, and advantages of the present disclosure will be apparent from reading the following description and claims, and from reviewing the accompanying drawings.

BRIEF DESCRIPTION OF THE DRAWINGS

Various example embodiments may be more completely understood in consideration of the following detailed description in connection with the accompanying drawings.

Figure 1:
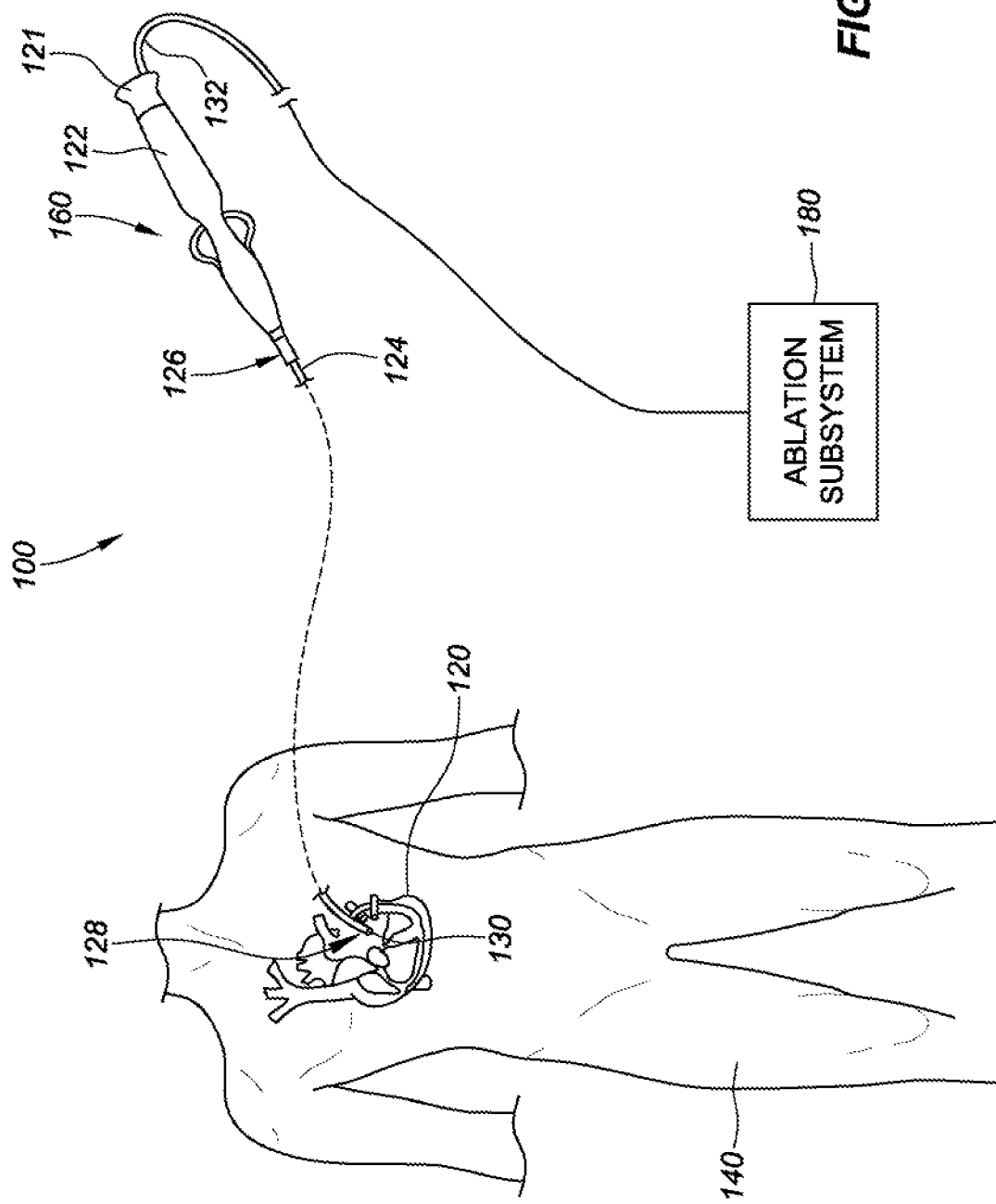
FIG. 1 is a schematic and diagrammatic view of a catheter system for performing a therapeutic medical procedure, consistent with various aspects of the present disclosure.

While various embodiments discussed herein are amenable to modifications and alternative forms, aspects thereof have been shown by way of example in the drawings and will be described in detail. It should be understood, however, that the intention is not to limit the scope to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION OF EMBODIMENTS

The instant disclosure relates to electrophysiology catheters for tissue ablation within the heart, other organs, and/or tissue within the body. In particular, the instant disclosure relates to an electrophysiology ablation balloon catheter with a combination of coated and uncoated regions for focusing ablative energy at target tissue. In some cardiac-related applications for treating atrial fibrillation, for example, pulmonary venous tissue is ablated to alleviate symptoms and/or cure the condition entirely. Various embodiments of the present disclosure are described below with specific reference to the figures. These embodiments are directed toward atrial fibrillation treatment, but may be readily applied to various other conditions and organs within a human body or animals.

Ablation therapies may be delivered by making a number of individual ablations in a controlled fashion in order to form a lesion line. Such lesion lines are often formed around/between the pulmonary veins in the left atrium of the heart which have been associated with the introduction of erratic electric signals into the heart. Various embodiments of the present disclosure are directed to minimizing the number of energy applications to the pulmonary veins. Other diagnostic catheters include hoop and balloon mounted designs with energy applying features; however, such designs suffer from a lack of ability to focus ablation energy at a target circumference and length of the pulmonary vein during therapy delivery. This results in energy loss to the blood pool and unintentional ablation of non-target tissue. Moreover, the resulting energy loss may reduce the efficacy of target tissue ablation, and cause inconsistent lesion lines and incomplete electrical signal blockage. In some cases, unintentional ablation of non-target tissue may cause pulmonary vein stenosis, phrenic nerve injury, and esophageal damage.

Balloon based ablation has been used for various therapeutic applications in the medical field, including pulmonary vein isolation (PVI) procedures. Several energy sources may be utilized within the balloon catheter to deliver therapeutic energy including radiofrequency (RF), ultrasound, laser, cryogenic and others. Aspects of U.S. Pat. Nos. 6,952,615, 7,112,198, 8,231,617, and 8,647,339, disclose various high frequency RF thermal balloon catheters which achieve ablation by heating the tissue in contact with the balloon, each of which are hereby incorporated by reference as though fully set forth herein. In various embodiments consistent with the present disclosure, lesions may be created through capacitive type heating where transmitted RF energy heats the tissue in contact with the balloon; however, large amounts of energy are lost through the non-tissue contacting areas of the balloon (e.g., blood pool). Various embodiments of the present disclosure improve energy delivery efficiency by focusing the transmission of RF energy to targeted pulmonary vein tissue (e.g., antrum and/or ostia). As a result, RF energy is only delivered to the target pulmonary vein, and not to the blood pool or other tissue—which could result in unwanted lesions. As the blood pool no longer functions as a large heat sink for such RF energy, the incidence for blood coagulation in the stagnant blood pool adjacent the ablation balloon may be greatly reduced.

In various embodiments, to improve the efficiency of the energy delivered through an ablation balloon, the balloon may be coated (e.g., insulated) in specific regions to reduce the energy dissipated through the non-tissue contacting areas of the balloon. In uncoated regions of the ablation balloon, energy may be transmitted with limited resistance. In specific embodiments, coating the balloon may have a dielectric effect. Specifically, desired lesion patterns can be generated by coating in a specific configuration around the balloon. The uncoated region may take various forms such as circumferential, longitudinal, or a spiral pattern that facilitates energy delivery only to a desired target tissue area. By mitigating extraneous RF energy delivery to non-target tissue, the risk of PV stenosis, phrenic nerve injury, and esophageal damage may be greatly reduced. Coating material may be insulating materials with high volume resistivity, high elongation to break, and/or similar durometer to the balloon upon which it is coated. Parylene is one example polymer coating which may be used. Parylene exhibits excellent dielectric properties, is chemically inert and a known biocompatible material. Silicone is another material which may be used for the coating. Parylene is a trade name for a variety of chemical vapor deposited poly(p-xylylene) polymers used as moisture and dielectric barriers. Parylene C, one of the varieties of parylene, has advantageous barrier properties that may be used as the coating material in various embodiments of the present disclosure.

Referring now to the drawings wherein like reference numerals are used to identify similar components in the various views, FIG. 1 is a schematic and diagrammatic view of a catheter ablation system 100 for performing a tissue ablation procedure. In the present embodiment, tissue 120 is myocardial tissue within a human body 140. It should be understood, however, that the system may find application in connection with a variety of other tissues within human and non-human bodies, and therefore, the present disclosure is not meant to be limited to the use of the system in connection with only myocardial tissue and/or human bodies.

Catheter ablation system 100 may include a catheter 160 and an ablation subsystem 180 for controlling an ablation therapy conducted by an ablation balloon 130 at a distal end of the catheter 160. The ablation subsystem 180 can control the application of and/or generation of ablative energy including, for example, radio frequency (RF), cryoablation, laser, chemical, and high-intensity focused ultrasound.

In the example embodiment of FIG. 1, catheter 160 is provided for examination, diagnosis, and/or treatment of internal body tissue, such as cardiac tissue 120. The catheter may include a cable connector or interface 121, a handle 122, a shaft 124 having a proximal end 126 and a distal end 128 (as used herein, "proximal" refers to a direction toward the end of the catheter 160 near the handle 122, and "distal" refers to a direction away from the handle 122), and an ablation balloon 130 coupled to the distal end of the catheter shaft 124.

In one example embodiment, ablation balloon 130 is manipulated through vasculature of a patient 140 using handle 122 to steer one or more portions of shaft 124, and position the ablation balloon at a desired location within heart 120. In various embodiments, the ablation balloon includes ablation elements (e.g., an RF coil, ablation electrodes, high intensity focused ultrasound ablation elements, etc.) that when operated by ablation subsystem 180 ablates the tissue 120 in contact with the ablation balloon 130 (and in some cases tissue 120 in proximity to the ablation balloon 130 may be ablated by conductive energy transfer through the blood pool to the proximal tissue).

In various specific embodiments of the present disclosure, catheter 160 may include electrodes and one or more positioning sensors at a distal end 128 of catheter shaft 124 (e.g., electrodes or magnetic sensors). In such an embodiment, the electrodes acquire electrophysiology data relating to cardiac tissue 120, while the positioning sensor(s) generate positioning data indicative of the three dimensional position of the ablation balloon 130. In further embodiments, the catheter 160 may further include other conventional catheter components such as, for example and without limitation, steering wires and actuators, irrigation lumens and ports, pressure sensors, contact sensors, temperature sensors, additional diagnostic electrodes, and corresponding conductors, leads, or traces.

Connector 121 provides mechanical and electrical connection(s) for one or more cables 132 extending, for example, from ablation subsystem 180 to ablation balloon 130 mounted on distal end 128 of catheter shaft 124. In other embodiments, the connector may also provide mechanical, electrical, and/or fluid connections for cables extending from other components in catheter system 100, such as, for example, a fluid source (when the catheter 160 comprises an irrigated catheter) and contact/pressure sensing circuitry. The connector 121 is conventional in the art and is disposed at a proximal end 126 of the catheter 160.

Handle 122 provides a location for a user to hold catheter 160 and may further provide steering or guidance for the shaft 124 within the body 140. For example, the handle 122 may include means to manipulate one or more steering wires extending through the catheter 160 to a distal end 128 of the shaft 124, thereby facilitating steering of the shaft. The handle 122 is conventional in the art and it will be understood that the construction of the handle may vary. In other embodiments, control of the catheter 160 may be automated by robotically driving or controlling the catheter shaft 124, or driving and controlling the catheter shaft 124 using a magnetic-based guidance system.

Catheter shaft 124 is an elongated, tubular, and flexible member configured for movement within a patient's body 140. The shaft supports an ablation balloon 130 at a distal end 128 of catheter 160. The shaft 124 may also permit transport, delivery and/or removal of fluids (including irrigation fluids, cryogenic ablation fluids, and body fluids), medicines, and/or surgical tools or instruments. The shaft 124, which may be made from conventional materials used for catheters, such as polyurethane, defines one or more lumens configured to house and/or transport electrical conductors, fluids, and/or surgical tools. The catheter may be introduced into a blood vessel or other structure within the body 140 through a conventional introducer sheath.

In one example of cardiac ablation therapy to correct for atrial arrhythmia, the introducer sheath is introduced through a peripheral vein (typically a femoral vein) and advanced into right atrium, in what is referred to as a transseptal approach. The introducer sheath then makes an incision in the fossa ovalis (the tissue wall between the left and right atriums), and extends through the incision in the fossa ovalis to anchor the introducer sheath therein. The ablation catheter 160 may then be extended through a lumen of the introducer sheath into the left atrium. Catheter shaft 124 of ablation catheter 160 may then be steered or guided through the left atrium to position an ablation balloon 130 into a desired location within the left atrium such as a pulmonary vein.

To achieve effective and efficient ablation of target myocardial tissue in contact with an ablation balloon 130, energy transfer through the ablation balloon must be focused in a way that limits energy transfer through portions of the balloon that are not in contact with the target myocardial tissue. For example, in an RF balloon application, an RF coil within the balloon emits an RF signal which is absorbed by not only the portion of the balloon in contact with the target tissue, but also the blood pool and non-target tissue. This unintentional energy loss impedes the effectiveness of the tissue ablation therapy, as energy applied to the target tissue is unknown, and heating efficiency of the RF coil is greatly impeded due to the various non-target heat sinks. Accordingly, aspects of the present disclosure focus energy transfer through the ablation balloon by implementing coated and uncoated regions on a surface of the balloon. The coated portions may be placed in areas where target tissue is unlikely to contact the surface of the ablation balloon and insulates these portions to prevent undesired energy transfer. The uncoated portions may be placed in areas where target tissue is likely to contact the surface of the ablation balloon, and facilitate energy transfer between the RF coil and tissue in contact with the uncoated portion of the ablation balloon—thereby focusing RF energy on the target tissue areas and reducing overall RF energy required for a given therapy.

In applications utilizing direct current electroporation pulses and/or radio frequencies to conduct tissue ablation therapy, the coated regions may help facilitate the flow of radio waves and/or electrical pulses through the uncoated regions. In such applications, the coated regions may act to shield non-target tissue from the radio waves and/or electrical pulses emanating from the ablation balloon. In some specific embodiments, the coated regions of the ablation balloon may reflect back the radio waves and/or electrical pulses emitted from within the ablation balloon and increase the intensity/strength of the resulting radio waves and/or electrical pulses emitted from the uncoated region(s) of the ablation balloon.

Figure 2:
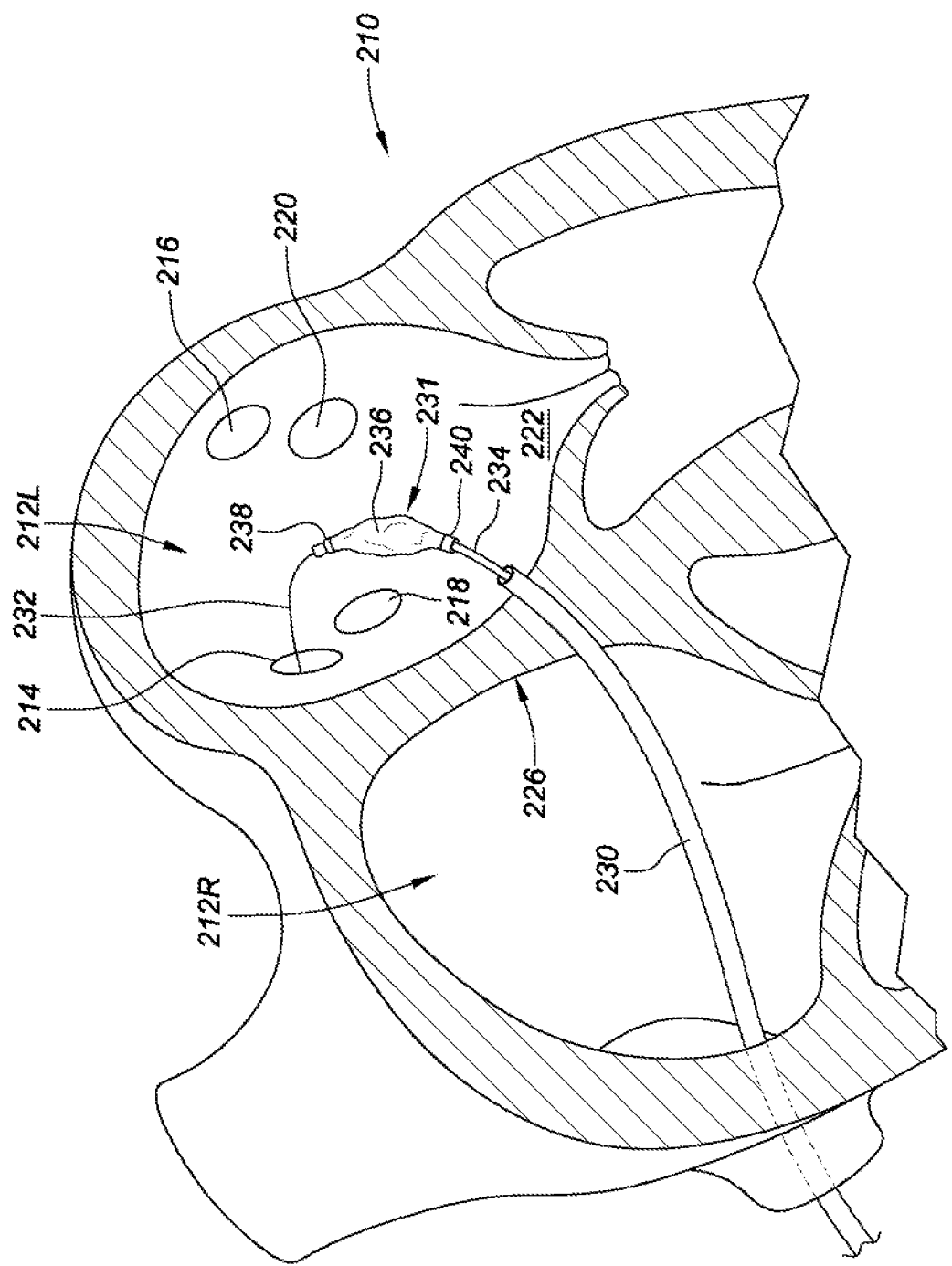
FIG. 2 is a cross-sectional front-view of a left atrium with an ablation balloon catheter locating a pulmonary vein, consistent with various aspects of the present disclosure.

FIG. 2 is a cross-sectional front-view of a portion of cardiac muscle 210 with an ablation balloon catheter 231 locating a pulmonary vein (e.g., 214, 216, 218, and 220) for performing ablation therapy. As shown in FIG. 2, the cardiac muscle 210 includes two upper chambers called the left atrium 212L and right atrium 212R, and two lower chambers called the left ventricle and right ventricle (partially visible).

Aspects of the present disclosure are directed to ablation therapies in which tissue in pulmonary veins 214, 216, 218, and 220, which form conductive pathways for stray electrical signals emanating from the pulmonary vein ostia, is destroyed in order to electrically isolate sources of unwanted electrical impulses (e.g., arrhythmogenic foci) located in the pulmonary veins. By either destroying the arrhythmogenic foci, or electrically isolating them from the left atrium 212L, the cause of atrial symptoms can be reduced or eliminated entirely.

As shown in FIG. 2, an ablation balloon catheter 231 may be introduced into the left atrium 212L by an introducer sheath 230. A guidewire and distal catheter shaft, 232 and 234, respectively, may guide the ablation balloon 236, once introduced into the left atrium 212L by the introducer 230. Optionally, the ablation balloon catheter 231 may include mapping electrodes at proximal and distal ends of ablation balloon, 240 and 238, respectively. In operation, introducer 230 has its distal end positioned within left atrium 212L. As shown in FIG. 2, a transseptal approach has been utilized in which introducer 230 is introduced through a peripheral vein (typically a femoral vein), advanced to right atrium 212R, and anchored to the wall of the fossa ovalis 226.

Ablation balloon catheter 234 may also be introduced into left atrium 212L through the arterial system. In that case, introducer 230 is introduced into an artery (such as a femoral artery) and advanced retrograde through the artery to the aorta, the aortic arch, and into the left ventricle. The ablation balloon catheter 234 is then extended from within a lumen of the introducer 230 to enter the left atrium 212L through mitral valve 222.

Once introducer 230 is in position within left atrium 212L, steerable ablation balloon catheter 231 is advanced out a distal end of the introducer 230 and toward one of the pulmonary veins (e.g., 214, 216, 218, and 220). In FIG. 2, the target pulmonary vein is right superior pulmonary vein 214. Guidewire 232 and a distal portion 234 of the ablation balloon catheter 231 are manipulated until the distal tip of the ablation balloon catheter is directed toward the target pulmonary vein 214.

Where the therapy is directed toward an antral portion of a pulmonary vein, ablation balloon 236 is deployed, and then extended into contact with the antrum. Alternatively, where the therapy is directed toward a pulmonary vein ostia, the ablation balloon is extended into the pulmonary vein. Carried near a distal end 238 of ablation balloon catheter 231, ablation balloon 236 remains in a collapsed condition so that it may pass through introducer 230, and enter into the target pulmonary vein 214. Once in position within the ostia, the ablation balloon 236 is deployed, so that it engages and secures the ablation balloon catheter 231 within the target pulmonary vein 214. In some applications, it may be desirable to occlude the flow of blood from the pulmonary vein into the left atrium. To confirm proper occlusion of the pulmonary vein, fluoroscopic dye may be injected into the blood pool within the pulmonary vein (and visible via fluoroscopic imaging)—where the fluoroscopic dye stagnates within the pulmonary vein, the ablation balloon is effectively occluding the pulmonary vein. Once proper position of the ablation balloon is verified, ablation therapy may be initiated.

In various embodiments, it may be desirable to minimize wall thickness of ablation balloon 236 to facilitate RF energy transfer between an RF coil within the ablation balloon and tissue in contact with an outer surface of the ablation balloon. In one specific embodiment, the ablation balloon thickness may be 0.0010"±0.0002" at an area surrounding the greatest diameter of the ablation balloon. A coated region applied to an exterior of the ablation balloon may vary between 0.002" to 0.005", for example. In some embodiments, the coating thickness may be limited as excessive coating may adversely affect the deployed shape of the balloon. In various embodiments, the ablation balloon may be a type of medical grade polyurethane, such as Pellethane®. In yet other embodiments, the ablation balloon may be comprised of a polyether block amide, such as Pebax®.

As optionally shown, the embodiment of FIG. 2 may include mapping electrodes 238 and 240. The mapping electrodes 238 and 240 may be ring electrodes that allow a clinician to perform a pre-deployment electrical mapping of the conduction potentials of the pulmonary vein 214. Although shown as being carried on ablation balloon catheter 231, mapping electrodes may alternatively be carried on-board a separate electrophysiology catheter. In various other embodiments, the electrodes may also be positioned on an outer surface of the ablation balloon 236. After an ablation therapy is complete, the clinician may utilize the mapping electrodes 238 and 240 to map the conduction potentials of the pulmonary vein to determine the efficacy of the ablation therapy.

To ablate tissue, once deployed, ablation balloon 236 may radiate a radio-frequency signal into the targeted tissue of the pulmonary vein 214. In other embodiments, the ablation balloon 236 may conduct a direct current into the target tissue to ablate (commonly referred to as electroporation). In yet other embodiments, the ablation balloon 236 may deliver one or more of the following energies to the targeted tissue: cryoablation, laser, chemical, and high-intensity focused ultrasound, among others.

In various embodiments consistent with the above implementations, ablation balloon 236 may also include one or more coated regions of the ablation balloon 236 that insulate, shield, resist, limit, or otherwise mitigate the flow of ablation energy there through. In specific implementations, the coated regions are aligned with tissue that is not targeted for ablation therapy; whereas un-coated regions of the ablation balloon 236 are positioned to contact tissue targeted for the ablation therapy and facilitate the flow of ablation energy there through.

Various ablation balloon implementations are envisioned including an ablation balloon for ablating an antral portion of a pulmonary vein. In such an embodiment, a distal portion of the ablation balloon may consist of an uncoated region for facilitating the transfer of ablative energy between the uncoated region of the ablation balloon and the pulmonary vein antrum. The proximal portion of the ablation balloon may consist of a coated region to prevent ablative energy from being directed away from the antrum by a blood pool heat sink and/or non-target tissue, for example. Yet other ablation balloon implementations consistent with the present disclosure are directed to ablating a pulmonary vein ostia. In such an embodiment, a central circumferential portion of the ablation balloon consists of an uncoated region for affecting ablation therapy to the ostia. The proximal and distal portions of the ablation balloon comprising coated regions to prevent the ablative energy from being directed away from the ostia by a blood pool heat sink and/or non-target tissue.

Figure 3:
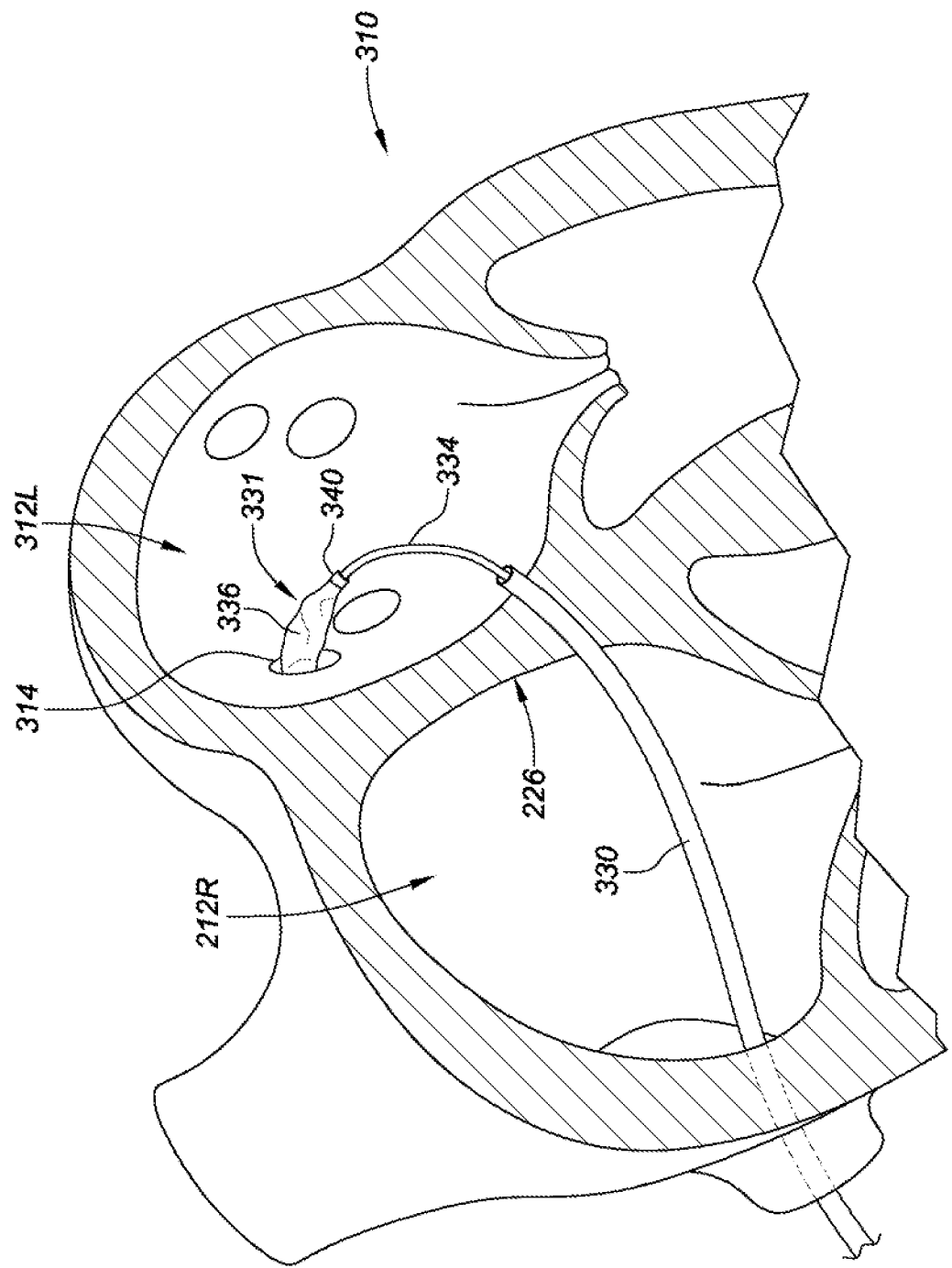
FIG. 3 is a cross-sectional front-view of a left atrium with an ablation balloon catheter positioned within a pulmonary vein, consistent with various aspects of the present disclosure.

FIG. 3 shows an ablation balloon catheter 331 including an ablation balloon 336 advancing through an antral portion of a pulmonary vein 314 and into an ostium (where the ostium is to receive the ablation therapy). To advance the balloon 336, catheter shaft 334 is extended out of introducer sheath 330. As discussed above, the introducer sheath delivers the ablation balloon catheter 331 to left atrium 312L via right atrium 212R and transseptal wall 226. As the ablation balloon catheter 331 enters the pulmonary vein 314, mapping may be conducted using electrodes, 338 (hidden from view) and 340, in order to verify proper location prior to deployment of the ablation balloon 336.

It has been discovered that augmenting ablation balloon 336 with a combination of coated and uncoated regions may facilitate precise energy transfer into/out of the ablation balloon 336. In various embodiments of the present disclosure, the coated and uncoated regions may be integral to the expandable ablation balloon (e.g., a material additive, or distinct materials that are fused together), coupled to an interior and/or exterior surface of the ablation balloon, comprise an additional/separate layer within the ablation balloon 336, or comprise one layer of a dual layer balloon set-up (e.g., a balloon positioned within an outer ablation balloon (or vice versa)). In yet further more specific embodiments, each of the coated and uncoated regions may comprise its own segment of a balloon that is free-standing relative to the other layer(s) and the expandable ablation balloon itself. In such embodiments, the coated and uncoated regions may be adjustable via a pull wire or other adjustment mechanism to vary the location of the coated and uncoated regions (e.g., coated and uncoated baffles). By dynamically adjusting the position of the coated and uncoated baffles, the focus of the energy transfer system of the ablation balloon 336 may be adjusted to various portions of a pulmonary vein in contact with the balloon. Such an embodiment facilitates, for example, sequential ablation therapies at antral and ostial portions of the pulmonary vein without re-positioning of the ablation balloon 336.

In one specific application, where a therapy is being conducted to treat a patient suffering from atrial fibrillation symptoms—an ablation balloon 336 (consistent with the present disclosure) engages inner walls of a target pulmonary vein 314. Once in position, coated baffles of the ablation balloon may be positioned to focus energy transfer using pull wires and/or steering wires extending the length of catheter shaft 334 between a catheter handle and balloon 336. For the first therapy, the coated baffles may be positioned to minimize transfer of energy through distal and proximal portions of the ablation balloon; accordingly, an uncoated region may be positioned near a central portion of the ablation balloon and is flanked by coated baffles both distal and proximal. This configuration may be implemented for ablating an ostium of the pulmonary vein. Using one or more of the energy transfer means discussed above, the ablation balloon focuses a transfer of energy at tissue of the pulmonary vein ostium, while minimizing energy transfer to other areas of the pulmonary vein tissue via the coated baffles which may shield, insulate, reflect, or otherwise mitigate the flow of energy through the coated regions. The therapy creates a circumferential zone of ablation around an inner wall of the pulmonary vein ostium. The ablation zone electrically isolates the target pulmonary vein 314 from left atrium 312L. To the extent that arrhythmogenic foci were located within the ablation zone, the arrhythmogenic foci are destroyed. To the extent the arrhythmogenic foci are located in the target pulmonary vein opposite the left atrium, the electrical impulses produced by those foci are blocked or substantially inhibited by the ablation zone.

After the ablation therapy at a pulmonary vein ostium is complete, the ablation balloon may be collapsed for removal from the cardiac muscle 310, or may be repositioned and/or reconfigured to conduct additional ablation therapies to other pulmonary veins and/or to other portions of the target pulmonary vein 314. For example, the coated baffles may be reconfigured and/or the ablation balloon 336 repositioned to conduct ablation therapy on an antral portion of the target pulmonary vein 314. In such an application, a distal portion of the ablation balloon may be positioned into contact with the antrum, and the coated baffles repositioned, via the guide wires, to the proximal portion of the ablation balloon. Using one or more of the energy transfer means discussed above, the ablation balloon focuses a transfer of energy at the antral portion of the pulmonary vein, while minimizing energy transfer into the blood pool and to other areas of the pulmonary vein tissue by shielding, insulating, reflecting, or otherwise mitigating the flow of energy via the coated baffles. The therapy creates a circumferential zone of ablation around the antral portion of the pulmonary vein that electrically isolates the target pulmonary vein 314 from left atrium 312L.

Figure 4:
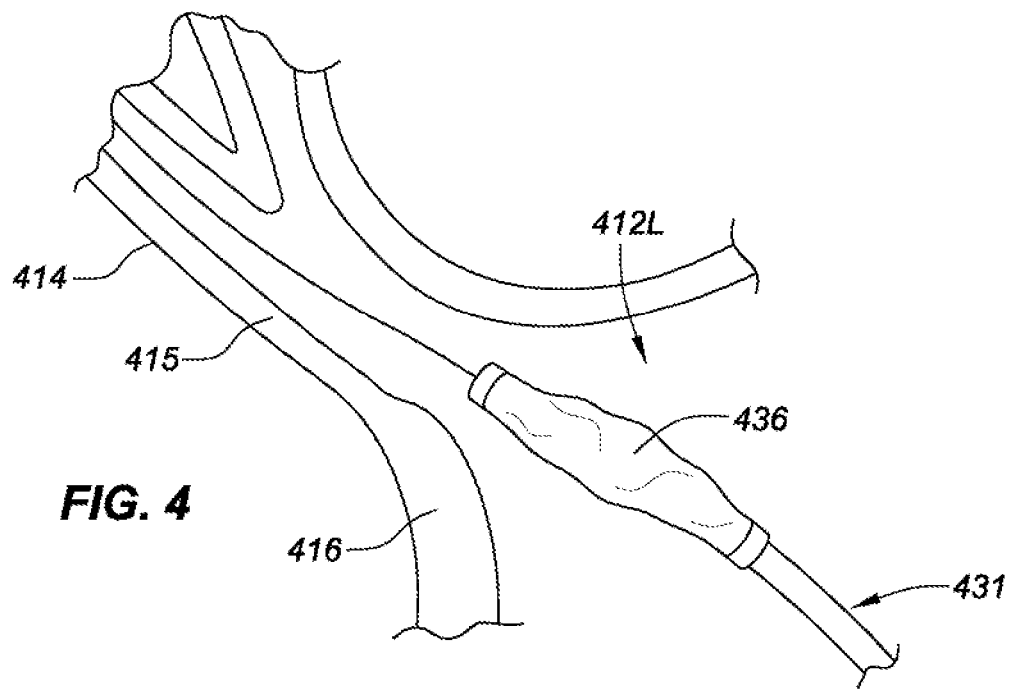
FIG. 4 is a cross-sectional front-view of a pulmonary vein with an ablation balloon catheter positioned therein, prior to deployment of the ablation balloon, consistent with various aspects of the present disclosure.

FIG. 4 shows an ablation balloon catheter 431 with ablation balloon 436 in position within target pulmonary vein 414 prior to balloon deployment. In the present embodiment, the ablation balloon catheter 431 is positioned to conduct an ablation therapy within an antrum 416 of the target pulmonary vein 414. In such a procedure, once the ablation balloon is expanded into contact with the antrum 416, an ablation therapy may be initiated that ablates a circumferential ring of ablation around the antrum 416. The circumferential zone of ablation electrically isolates the left atrium 412L from electrical impulses produced by arrhythmogenic foci opposite the ablation. In some embodiments of the present disclosure, precisely locating the ablation balloon catheter 431 may greatly affect the efficacy of the ablation therapy; accordingly, some embodiments of the present disclosure properly locate the ablation balloon within the target pulmonary vein 414 by mapping, prior to deployment of the ablation balloon, using electrodes proximal and distal the ablation balloon 436. In yet other embodiments, the ablation balloon 436 may be positioned in contact with an ostium 415 of target pulmonary vein 414, to conduct an ablation therapy to the ostium.

Figure 5:
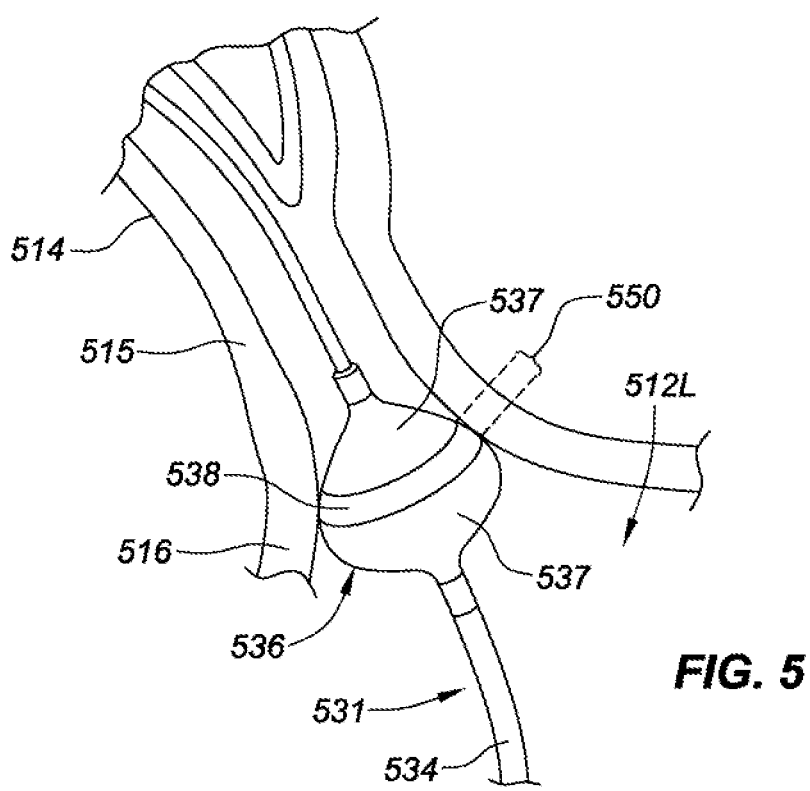
FIG. 5 is a cross-sectional front-view of a pulmonary vein with an ablation balloon catheter deployed therein, consistent with various aspects of the present disclosure.

FIG. 5 shows an ablation balloon catheter 531 with an expanded ablation balloon 536 engaged within an antrum 516 of target pulmonary vein 514. The expanded shape of the ablation balloon 536 may contour to a length and circumference of the pulmonary vein 514. Aspects of the present disclosure are directed to the ablation balloon 536 including a combination of coated and uncoated regions, 537 and 538, respectively. In one embodiment, the ablation balloon is an RF ablation balloon with an RF emitter (e.g., an RF coil) within the balloon that radiates RF energy into tissue in contact with the balloon (and in some circumstances, tissue in proximity to the ablation balloon), thereby ablating the tissue. The uncoated region 538 may be located around a central circumference of the ablation balloon 536. To facilitate ablation of tissue in contact with the uncoated region 538, an RF emitter within the balloon transfers RF energy through the balloon to a portion of the antrum 516 in contact with the uncoated region 538. The ablation balloon also includes coated regions 537 on the proximal and distal ends of the balloon that insulate these portions of the ablation balloon. The coated regions 537 prevent the transfer of RF energy to non-target areas of the pulmonary vein (e.g., ostia 515, in the present embodiment) and the blood pool surrounding the ablation balloon 536. Coated regions 537 increase the efficiency of energy delivery by the ablation balloon 536, which would otherwise be at least partially absorbed by the ostium 515 (and other non-target tissue), and the blood pool. Accordingly, such an ablation balloon design reduces ablation therapy times given the improved power efficiencies, or may produce enhanced zones of ablation 550 while maintaining therapy times. Moreover, in applications using other ablation means, such as cryoablation or direct current electroporation pulses, the coated regions 537 may radiate the generated energy back into the ablation balloon 536 in such a way as to achieve focusing and/or amplification of the energy through uncoated region 538.

Once ablation therapy is complete, ablation balloon 536 may be collapsed, and ablation balloon catheter 531 may be retracted back into introducer sheath 330 (see, e.g., FIG. 3). An electrophysiology catheter, or electrodes proximal and distal to the ablation balloon 536 (for example), may be used to verify the efficacy of the therapy prior to removal of the ablation balloon catheter 531. In various embodiments of the present disclosure, additional electrodes may also be positioned on a surface of the ablation balloon 536, either alone, or in conjunction with electrodes 238 and 240 (as shown in FIG. 2). Moreover, these various electrodes may be used before, during, and after the ablation therapy. For example, prior to the ablation therapy, the electrodes may be used to determine optimal positioning of the balloon to increase electrical isolation of the target pulmonary vein 514 from the left atrium 512L. During the ablation therapy, the electrodes may be used to track the ablation efficacy. Specifically, the sensed data from the electrodes may be used to determine when sufficient isolation between the pulmonary vein and the left atrium has been accomplished, and subsequently ending the ablation therapy. Similarly, after completion of an ablation therapy, the electrodes may be used to determine the efficacy of the ablation therapy (e.g., based on ablation lesion characteristics such as depth and surface area, as well as resistance to electrical stimulus), and whether additional therapy applications may be required.

In a typical ablation therapy, all pulmonary veins are treated. The processes as described herein for right superior pulmonary vein 214 may be replicated for each of the three other pulmonary veins Ablation balloons have been developed for a variety of different applications and take a number of different forms. Aspects of the present disclosure may utilize ablation balloons of various types and mechanical construction. The ablation balloons can be either self-erecting or mechanically erected, such as through the use of an internal balloon. In one example embodiment, a lumen extending through a length of a shaft 534 of the ablation balloon catheter 531 may inject a fluid into the ablation balloon which exerts a radial force on the ablation balloon—thereby expanding the balloon into an erect configuration (as shown in FIG. 5). Moreover, the uncoated and coated regions (538 and 537, respectively) of the balloon 536 may comprise various patterns, arrangements, and configurations across a surface of the ablation balloon as desirable for a given application or treatment. While various embodiments of the present disclosure have been directed to the treatment of atrial fibrillation within pulmonary veins of a human heart, aspects of the present disclosure are not to be construed so narrowly, but may instead be applied to various types of tissue, organs, and organisms.

Some embodiments may not require coated regions where the balloon material insulates the transmission of energy through the balloon. In such embodiments, the coating may instead be electrically and/or thermally conductive in nature, thereby facilitating transmission of energy to tissue in contact therewith and being applied to areas of the balloon where such energy transmission is desirable. It is further understood that aspects of the present disclosure may be directed to various implementations where the uncoated and coated regions (538 and 537, respectively) are integral to the expandable ablation balloon 536, applied to inner and/or outer surfaces of the ablation balloon 536, and/or positioned within an interstitial space between the expanded ablation balloon 536 and catheter shaft 534.

Figure 6A:
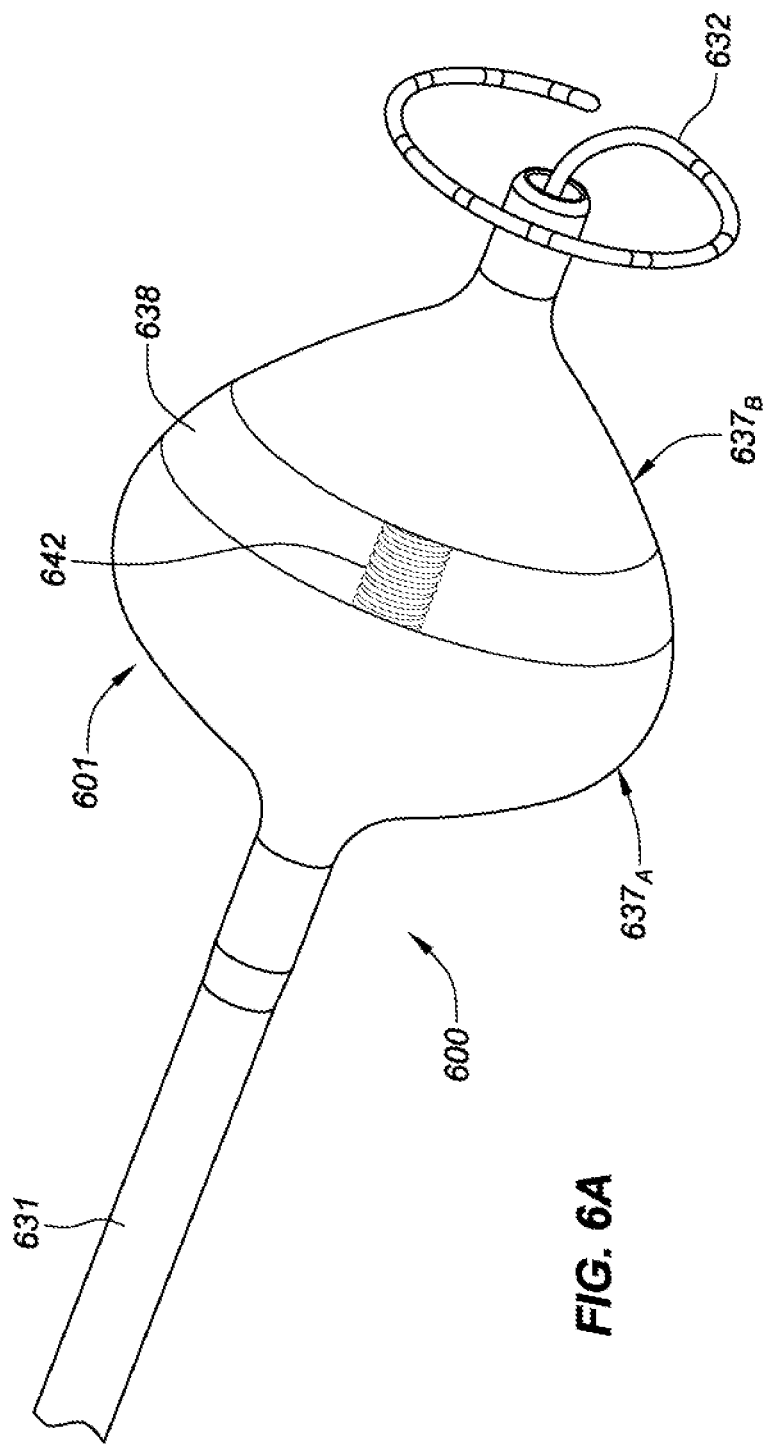
FIG. 6A is an isometric side view of a deployed ablation balloon catheter and an electrophysiology loop catheter extending through a central lumen of the ablation balloon catheter, consistent with various aspects of the present disclosure.
Figure 6B:
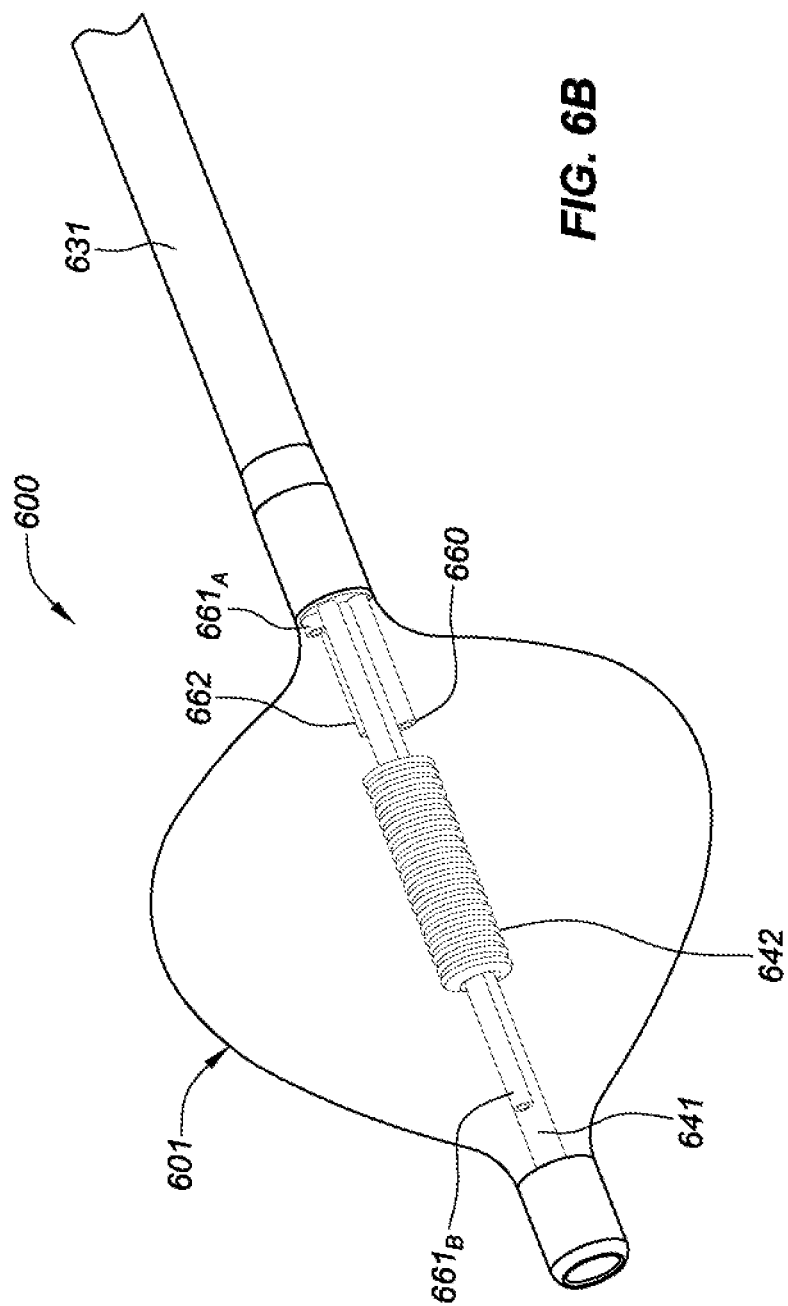
FIG. 6B is an isometric side view of the deployed ablation balloon catheter of FIG. 6A with the balloon shown in transparency, consistent with various aspects of the present disclosure.

FIG. 6A is an isometric side view of a deployed ablation balloon catheter 600 with an electrophysiology loop catheter 632 extending through a distal end of a central lumen 641 (as shown in FIG. 6B) of the ablation balloon catheter, consistent with various aspects of the present disclosure. Ablation balloon 601 is coupled to a distal end of a catheter shaft 631 of the ablation balloon catheter 600. A central lumen 641 extends from a proximal to a distal end of the catheter shaft 631 and through the ablation balloon 601. The central lumen facilitates the use of the electrophysiology loop catheter 632 to retrieve electrophysiological data related to tissue adjacent the ablation balloon 601. In some applications, electrophysiology catheters may be positioned on either side of the ablation balloon 601 and facilitate collection of electrophysiological characteristics of the pulmonary vein to establish information including the efficacy of an ablation therapy. In one specific embodiment, one of the electrophysiology catheters may be used as a reference while the other provides data indicative of the electrical signals received by the left atrium of the heart, for example.

The ablation balloon catheter 600 of FIG. 6A is fitted with an RF coil 642 for emitting radio frequencies waves with sufficient power to ablate tissue in proximity to the ablation balloon 601. However, RF coils 642 lack the ability to target or otherwise focus RF energy emitted from the coil. Moreover, while a total energy output of the RF coil 642 may be known, it is difficult to ascertain how much of that energy is actually absorbed by the tissue being ablated—as a substantial amount of the energy may be absorbed by the blood pool or non-target tissue in proximity to the balloon. Accordingly, various embodiments of the present disclosure are directed to ablation balloons 601 including a combination of coated and uncoated regions, 637 and 638. The coated regions 637 may have material properties including reduced thermal transmission, and/or electrical conductivity, which reduce or eliminate the transmission of energy to tissue and blood in contact with the coated regions 637. Specifically, in an ablation therapy procedure targeting the antrum of the pulmonary vein, the uncoated region 638 (shown in transparency) is positioned on the balloon between two coated regions 637 to help direct the transfer of RF energy only to the antrum. In such a procedure, the distal coated region $637^B$ may be in contact with an ostium of the pulmonary vein as well as an occluded blood pool. Similarly, the proximal coated region $637^A$ may be in contact with a blood pool within the left atrium of the heart and perhaps an additional area of the antrum. The coated regions reduce or eliminate a flow of RF energy (or other types of energy depending on the energy delivery methodology of the ablation balloon) to the tissue in contact therewith, preventing ablation of such tissue during the ablation therapy. Moreover, the blood pool in contact with the coated regions is further prevented from coagulation due to extreme heating and/or charring on the balloon surface. It is to be understood that the coating need not be limited to an outer, inner, or interstitial space between one or more balloons 601. Instead, the coating may comprise an independent structure comprising materials that facilitate the focusing of the energy from the RF coil 642. In yet further more specific embodiments, the coating may be applied directly to the RF coil 642 itself, and/or independent energy-focusing structures, and/or coated portions 637 of the ablation balloon 601. Some embodiments may impregnate the ablation balloon itself with material compositions that facilitate energy shielding in select portions of the ablation balloon 601. Embodiments may also utilize RF coils 642 that have selective/focused energy emission beams. By precisely positioning the RF coil 642 along the exterior of the center lumen 641, the focused beam of the RF coil 642 may be directed at a target tissue while mitigating damage to non-target tissue.

In FIG. 6A, coated regions of the balloon $637^A$ and $637^B$ are shown as opaque, while uncoated region of the balloon 638 is shown in transparency. It is to be understood that the various coated and uncoated regions of the balloon may be either transparent or opaque, as desired, or as controlled by the material properties of at least the balloon material and/or the coating material.

RF coil 642 may be electrically coupled to a radio frequency signal generator which generates a signal indicative of desired radio frequency waves. Upon receiving the signal from the signal generator, the RF coil 642 transmits radio frequency waves through a fluid within the balloon and the uncoated region 638 of the ablation balloon to ablate tissue in contact with the uncoated region. The signal generator may be located adjacent a proximal end of catheter shaft 631 and electrical leads extending a length of the catheter shaft may electrically couple the RF coil 642 to the signal generator.

FIG. 6B is an isometric side view of the deployed ablation balloon catheter 600 of FIG. 6A with balloon 601 shown in transparency. To facilitate transport of the ablation balloon catheter 600 through an introducer and into position with a pulmonary vein, the ablation balloon 601 is transported in a collapsed configuration. Prior to an ablation therapy, the ablation balloon 601 may be inflated using a gas or liquid that is delivered to the ablation balloon through proximal outlet $661^A$ and distal outlet $661^B$ (other embodiments may have more or less outlets, or may utilize the same outlet for both inflation and deflation of the ablation balloon). The introduction of a fluid within the ablation balloon exerts a radial force that expands the balloon. Similarly, when an ablation therapy is complete, the balloon 601 may be deflated by drawing fluid within the ablation balloon out through an inlet 660 that is fluidly coupled to a lumen 641 that extends the length of the catheter shaft 631. In yet other embodiments, the ablation balloon may include a deformable structure that facilitates expansion of the ablation balloon upon exiting the introducer and/or upon activation of a control wire. Such an embodiment may reduce the complexity of the ablation balloon catheter by eliminating the need for fluid flow through the catheter shaft to trigger inflation and deflation of the balloon.

The same fluid used to inflate/deflate the balloon 601 may also be conductive. Accordingly, the conductive fluid (e.g., saline solution) may be used to transport a radio-frequency signal generated by an RF coil 642 (within the balloon) to an uncoated region of the ablation balloon. As the uncoated region of the ablation balloon facilitates energy transfer, the energy flows through the uncoated region and into contact with target tissue.

For facilitating enhanced control of the ablation therapy, the ablation balloon may be configured with a thermocouple 662 that measures a temperature of the fluid within the ablation balloon 601. The temperature of the fluid within the ablation balloon 601 will have at least some correlation to a temperature of tissue in contact with the ablation balloon 601, thereby facilitating data feedback to improve the efficacy of an ablation control system.

In various embodiments consistent with the present disclosure, an uncoated region of the ablation balloon may be located distal of a centerline of the ablation balloon. The size and shape of the balloon, in conjunction with the distal positioning of the uncoated region, facilitates ablation of an antral portion of a pulmonary vein.

Figure 7:
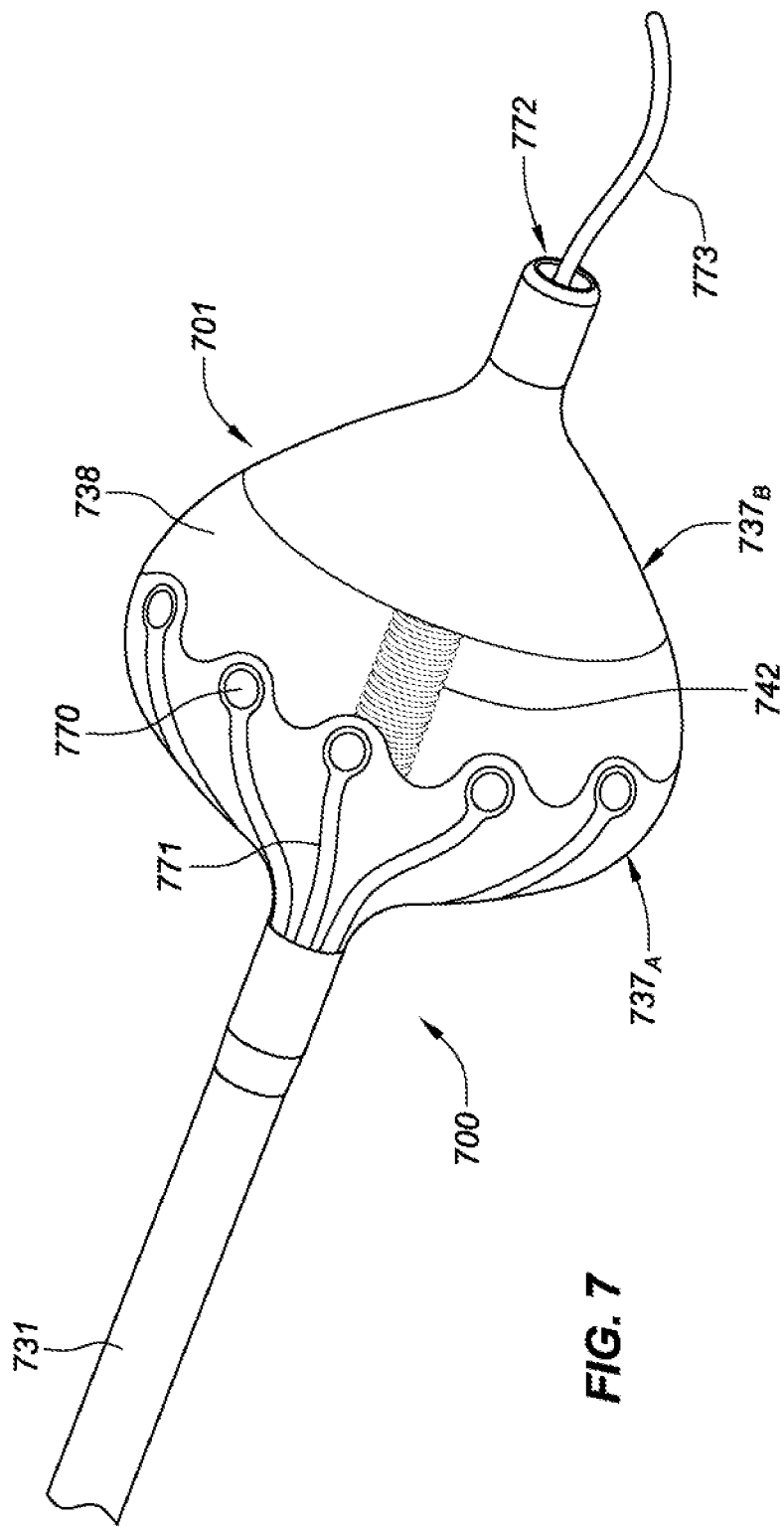
FIG. 7 is an isometric side view of a deployed ablation balloon catheter and a guidewire extending through a central lumen of the ablation balloon catheter, consistent with various aspects of the present disclosure.

FIG. 7 is an isometric side view of a deployed ablation balloon catheter 700 and a guidewire 773 extending out a distal end of a central lumen 772 of the ablation balloon catheter. An ablation balloon 701 extends from a distal end of catheter shaft 731. The ablation balloon 701 includes an uncoated surface region 738 which is sandwiched in between a proximal coated region $737^A$ and a distal coated region $737^B$. When placed into contact with a pulmonary vein, the distal coated region $737^B$ is abutted to an ostium of the pulmonary vein (and an occluded blood pool), the uncoated surface region 738 is in contact with a target area of an antrum, and the proximal coated region $737^A$ is touching a non-target area of the antrum (and a blood pool within the left atrium). During the ablation therapy, the coated regions reduce or entirely eliminate the flow of RF energy therethrough, while the uncoated region facilitates RF energy transmission to the targeted area of the antrum. The present embodiment also includes one or more flexible electronic circuits extending over a surface of the ablation balloon 701. The flexible electronic circuit includes one or more multi-flex diagnostic electrodes 770 circumferentially distributed about the proximal end of the ablation balloon. Each of the multi-flex diagnostic electrodes 770 are electrically coupled to lead wires within catheter shaft 731 via electrical traces 771 extending along the surface of the balloon. When properly positioned, one or more of the multi-flex diagnostic electrodes 770 are placed into contact with tissue in close proximity to the ablated tissue. Before, during, and after the ablation therapy, the multi-flex diagnostic electrodes 770 receive electrophysiological signals indicative of the health of the tissue in contact therewith. Specifically, for example, in atrial fibrillation patients, the pulmonary veins deliver undesirable electrical signals that can lead to erratic beating of one or more chambers of the heart (often out of sync with the other chambers). The ablation therapy creates lesioned tissue where the uncoated region 738 contacts the antrum. When the ablation therapy is effective, the lesioned tissue is less capable of conducting electrical signals, thereby disrupting undesirable electrical pathways and limiting or preventing stray electrical signals that would otherwise lead to the arrhythmia. Controller circuitry, based upon the electrophysiological data received from the multi-flex diagnostic electrodes 770, may determine the efficacy of the ablation therapy, whether additional ablations are required, and/or whether to prematurely end an ablation therapy due to sufficient disruption of electrical signals from the pulmonary vein.

Multi-flex diagnostic electrodes 770, as shown in FIG. 7, may include temperature sensors. The electrodes may be positioned within the coated region, but in close proximity to the uncoated region, or be within the uncoated region. Various embodiments may utilize flexible circuitry to electrically couple the electrodes to lead wires within the catheter shaft and to facilitate the inflation and deflation of the balloon. In many embodiments, the electrodes are only for electrophysiological mapping and temperature monitoring, not for ablation. Temperature measurements at the electrode-tissue interface may provide feedback to the ablation controller and may be used to titrate the power to a preset energy level.

As shown in FIG. 7, a border between proximal coated region 737A and uncoated region 738 undulates about a circumference of ablation balloon 701. This undulation of the border allows one or more multi-flex diagnostic electrodes 770 to extend out onto a peninsula of coated region $737^A$. Each diagnostic electrode 770 being effectively surrounded by tissue targeted for ablation. The location of the diagnostic electrodes 770 on the coated region peninsula insulates the diagnostic electrodes from the RF signals emitted from RF coil 742, while placing the diagnostic electrodes 770 in close proximity to the tissue targeted for ablation (e.g., for receiving electrophysiological signals indicative of the health of the target tissue).

In variations to the embodiment shown in FIG. 7, one or more multi-flex diagnostic electrodes 770 may be coupled to an uncoated surface region 738 of balloon 701, or located partially extending across a plane defining a border between coated region $737^A$ and the uncoated surface region 738. Such positioning may facilitate direct contact between the diagnostic electrodes 770 and target tissue for ablation (e.g., tissue in contact with uncoated surface region 738). As a result, the diagnostic electrodes 770 may receive electrophysiological signals indicative of the health of the target tissue.

Figure 8:
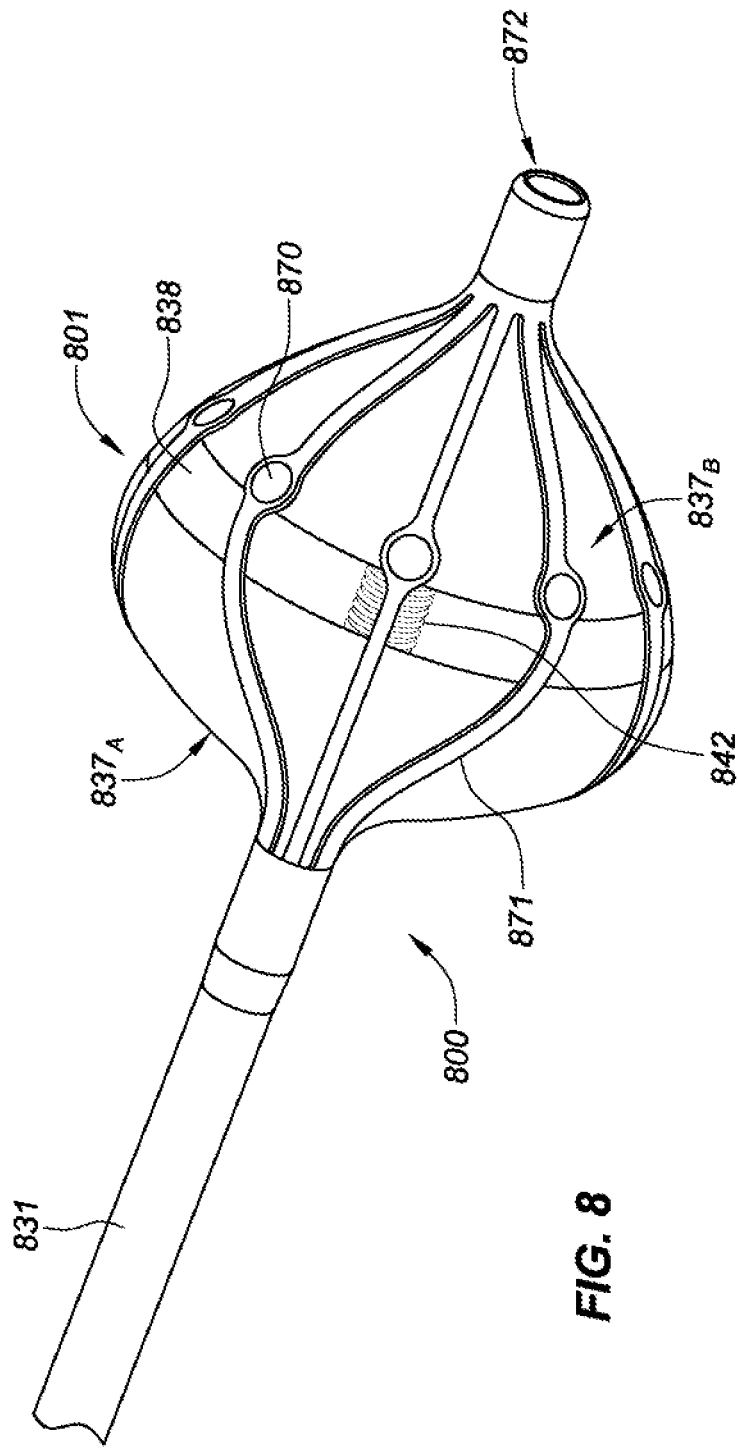
FIG. 8 is an isometric side view of a deployed ablation balloon catheter, consistent with various aspects of the present disclosure.

FIG. 8 is an isometric side view of a deployed ablation balloon catheter 800, consistent with various aspects of the present disclosure. The ablation balloon catheter 800 includes a catheter shaft 831 with an ablation balloon 801 extending from the distal end of the catheter shaft. Similar to FIG. 7, a central lumen 872 extends from a proximal end of the catheter shaft 831 to a distal end of the ablation balloon 801. The central lumen 872 facilitates the use of additional catheters on a distal end of the ablation balloon 801. The ablation balloon 801 includes one or more coated regions $837^A$, $837^B$ and one or more uncoated regions 838. The locations of the uncoated and coated regions on the ablation balloon 801 are dependent upon various factors, such as the preferred anatomical location of the ablation, dimensional characteristics of the tissue being ablated, the desired ablation lesion area (which is at least partially dependent on the severity of the condition), among other factors.

In the present embodiment, the dimensions of the ablation balloon and profile are configured to mate with an antrum of a patient's pulmonary vein. While it is desirable for the uncoated region 838 of the ablation balloon 801 to have continuous and consistent contact around a circumference of the pulmonary vein antrum to facilitate a complete and consistent ablation of the antrum, the coated regions $837^A$, $837^B$ may or may not be configured to contact the pulmonary vein tissue. In some embodiments it may be desirable for the coated regions $837^A$, $837^B$ to closely follow the curvature of the pulmonary vein to better seat the ablation balloon 801 within the pulmonary vein. However, in other embodiments it may be desirable to further insulate the coated regions $837^A$, $837^B$ of the ablation balloon 801 by allowing a small gap between the coated regions and the non-target tissue of the pulmonary vein. This small gap may allow for blood to pool there between, providing further insulation and a heat-sink between the energy source of the ablation balloon (e.g., RF coil 842) and the non-target tissue—preventing excessive/undesired tissue ablation.

The ablation balloon 801 of the present disclosure further includes an electrode support structure 871 that extends over a surface of the ablation balloon and supports multi-flex diagnostic electrodes 870 positioned distal of the uncoated region 838. The electrode support structure 871 may be integrated with the ablation balloon 801, or independent therefrom. In some embodiments, the ablation balloon and the electrode support structure 871 may be expanded by introducing a fluid into a chamber within the ablation balloon. In other embodiments, the electrode support structure 871 may be integral to the ablation balloon and have a structural bias that expands the balloon upon exiting an introducer, for example. When the ablation balloon 801 is expanded into contact with tissue, the multi-flex diagnostic electrodes 870 are also pressed into contact with the tissue. Accordingly, the multi-flex diagnostic electrodes 870 may transmit electrical signals to controller circuitry at a proximal end of the catheter shaft 831 indicative of electrophysiological characteristics of the target tissue. Electrical traces or lead wires from the multi-flex diagnostic electrodes 870 may be integrated within the electrode support structure 871, or may extend along one or more surfaces of the electrode support structure 871, and then through a lumen within the catheter shaft 831 to a handle at the distal end of the catheter shaft.

Multi-flex diagnostic electrodes 870 may be utilized to measure potentials across ablated tissue. Where the electrodes include temperature sensors, the sensed temperature at the electrode-tissue interface may be used to monitor the heating and to control the power output from a high-frequency RF generator during ablation. By focusing the generated energy of the RF coil on targeted tissue and limiting the transfer of energy to the blood pool and non-target tissue via strategically positioned coated regions on the balloon, ablation therapy power may be reduced by up to 50% with comparable ablation lesion depth. Similarly, where ablation therapy power is maintained, RF exposure periods may be greatly reduced with comparable ablation lesion depths.

In FIG. 8, multi-flex diagnostic electrodes 870 extend distally past an uncoated region 838 of the ablation balloon 801. However, in some variations to the embodiment shown in FIG. 8, the electrode support structures 871 may position the multi-flex diagnostic electrodes 870 directly above the uncoated region 838, distal or proximal the uncoated region, or over a plane defining a border between the uncoated region 838 and one of the coated regions $837^A$, $837^B$. Similar to the border between the proximal coated region 737A and coated region 738 shown in FIG. 7, the one or more borders between the uncoated region 838 and the coated regions $837^A$, $837^B$ may undulate about a circumference of the ablation balloon 801.

In some embodiments, the coated and uncoated regions of the ablation balloon need not be symmetrical, but may be asymmetrical to account for structural characteristics of the tissue structure being ablated. For example, the uncoated region may be larger in an area where consistent contact between the ablation balloon is unlikely due to unique topography that does not map well with the profile of the ablation balloon. Similarly, where electrophysiology mapping of a pulmonary vein, for example, indicates that a particular side or portion of the pulmonary vein is more conductive (e.g., delivers more stray electrical signals to the left atrium), the length of the uncoated region 838 to be aligned with such portions may be longer to increase the resistivity of the ablation in that region of the pulmonary vein. The thickness of the coated regions $837^A$, $837^B$ may also vary where less abrupt ablation lesions are desired, or where a particular contact point between the ablation balloon and the tissue may result in increased energy transfer (e.g., higher contact pressure).

In various embodiments, multi-flex diagnostic electrodes 870 need not be circumferentially aligned with one another, but may instead be offset to form one or more circumferential rings—facilitating electrophysiological readings along a length of the pulmonary vein. Such an embodiment may facilitate a more complete electrophysiological map of both the ablation lesion and the tissue adjacent thereto. In yet further more specific embodiments, the electrode support structure 871 may also include spot electrodes that may conduct spot ablations in areas where an electrophysiological mapping by the multi-flex diagnostic electrodes 870 indicates incomplete blockage of stray electrical signals after an ablation therapy. Such spot electrodes may utilize, for example, irreversible electroporation techniques, among others. The electrode support structure 871 may further facilitate pressure sensors that indicate to a clinician proper seating of the ablation balloon 801 within a pulmonary vein. In automated embodiments, the control system may not conduct an ablation therapy until a sufficient number of pressure sensors indicate contact with the pulmonary vein tissue—facilitating proper occlusion of the pulmonary vein.

All of the embodiments discussed herein may be readily adapted for use with cryoablation balloons. In such embodiments, the coating in the coated regions may include material properties that facilitate reduced thermal heat transfer, thereby insulating the tissue in contact with the coated regions from the cooling of the cryofluid within the ablation balloon. The cryofluid, in response to a rapid pressure change as it enters the ablation balloon, undergoes a phase change from liquid to gas that requires a large amount of energy—thereby drawing energy from the pulmonary vein in thermal communication thereto—ablating the tissue in contact with the uncoated region(s) of the balloon. To assist in focusing energy absorption by the ablation balloon, adjacent either side of uncoated regions, coated regions of the ablation balloon insulate the tissue and blood pool in proximity thereto to prevent heat transfer which may cause unintentional/over ablation of pulmonary vein tissue. Such coated regions also focus the energy absorption of the cryofluid phase change toward the target tissue, and mitigate heat transfer variations that may affect the overall efficacy of the ablation therapy, as well as decrease cryofluid use for a given ablation therapy. In various embodiments, the cryoablation balloon may include a cryo distribution manifold that may be positioned in such a way as to focus the cryofluid at specific regions of the ablation balloon 701—for example, the manifold may direct the cryofluid toward an uncoated region of the ablation balloon to further limit cooling of tissue in contact with the coated regions.

Aspects of the present disclosure are directed to an electroporation ablation balloon which utilizes direct current applied across target pulmonary vein tissue to ablate tissue. In such embodiments, distal and proximal portions of the ablation balloon comprise coated regions with material characteristics such as being electrically insulative. The uncoated region having a low electrical resistance that facilitates the flow of electrical current from the ablation balloon to tissue in contact therewith. In yet further embodiments, a fluid used to inflate the ablation balloon may be a conductive fluid, such as a saline solution. An electroporation pulse generated by a source (which may be within the ablation balloon) may transmit the pulse through the conductive fluid in the ablation balloon, and into contact with tissue in contact with the uncoated region of the ablation balloon.

In various embodiments of the present disclosure, an ablation balloon can be integrated onto a shaft of an electrophysiology hoop catheter (also referred to as a loop catheter). In yet other embodiments, an ablation balloon catheter may include a central lumen that allows for an electrophysiology hoop catheter to extend through the length of the ablation balloon catheter.

Embodiments consistent with the present disclosure may include ablation balloons that utilize radio frequency ablation techniques. In such embodiments, a radio frequency emitter may be located within the ablation balloon, such as in contact with a catheter shaft. The emitter (e.g., RF coil) transmits radio frequency waves through a fluid within the ablation balloon, an uncoated region of the ablation balloon, and into contact with tissue coupled with the uncoated region. In some embodiments, the uncoated portion is merely a polymer that allows for the transmission of radio waves. In various embodiments, where selective radiation of tissue with the radio waves is desirable, the coated portions of the ablation balloon may be, or include radio wave shielding materials that prevent the transmission of radio waves through the coated regions—thereby facilitating selective radiation and ablation of tissue.

In one embodiment, consistent with the present disclosure, an ablation balloon may have approximately 30% of its exterior surface uncoated, and approximately 70% of its surface coated. The coated region of the balloons may include areas where power delivery is undesirable, while simultaneously increasing the power density delivered to the uncoated area of the balloon. In a specific ablation balloon embodiment, the balloon has a diameter of 22 millimeters ("mm"), and a resulting total external surface area of approximately 1519 mm². Accordingly, the coated surface area is approximately 1063 mm² and the uncoated surface area is approximately 456 mm². Where 100 Watts is applied to a radio frequency emitter within the ablation balloon, the power density delivered to tissue in contact with the uncoated region is 1 Watt/4.5 mm², compared to 1 Watt/15 mm² in a balloon without such a coating. Accordingly, by selectively coating regions of the ablation balloon that come in contact with tissue and/or a blood pool where ablation is not desired, the power density delivered to target tissue for ablation may be increased 3.3 times. Table 1 below shows the test results from an example ablation therapy using an ablation balloon without coating regions (prior art), and Table 2 shows test results from an example ablation therapy using an ablation balloon including a coated region. As evident therefrom, ablation balloons consistent with the present disclosure may achieve similar ablation therapy results in the same length of therapy as the prior art balloon while greatly reducing energy applied to the RF electrode (50% or more).

TABLE 1

Uncoated RF Ablation Balloon Catheter

| Test # | Flow rate (ml/min) | Power (W) | Temp (° C.) RF Coil | Time (sec) | Lesion Depth (mm) |
|---|---|---|---|---|---|
| 1 | 17 | 100 | 81 | 240 | 2-5 |
| 2 | 17 | 120 | 84 | 240 | 3-5 |
| 3 | 17 | 120 | 88 | 240 | 2-5 |
| 4 | 17 | 130 | 87 | 240 | 4-5 |
| 5 | 17 | 130 | 86 | 240 | 2-4 |

TABLE 2

Coated/Uncoated RF Ablation Balloon Catheter

| Test # | Flow rate (ml/min) | Power (W) | Temp (° C.) RF Coil | Time (sec) | Lesion Depth (mm) |
|---|---|---|---|---|---|
| 1 | 12 | 60 | 70 | 240 | 3-5 |
| 2 | 12 | 60 | 68 | 240 | 2-5 |
| 3 | 12 | 60 | 69 | 240 | 3-5 |
| 4 | 12 | 60 | 65 | 240 | 3-4 |
| 5 | 12 | 65 | 64 | 240 | 3-6 |
| 6 | 12 | 60 | 65 | 240 | 4-5 |
| 7 | 12 | 60 | 68 | 120 | 4-6 |

Based upon the above discussion and illustrations, those skilled in the art will readily recognize that various modifications and changes may be made to the various embodiments without strictly following the exemplary embodiments and applications illustrated and described herein. Such modifications do not depart from the true spirit and scope of various aspects of the disclosure, including aspects set forth in the claims.

Although several embodiments have been described above with a certain degree of particularity to facilitate an understanding of at least some ways in which the disclosure may be practiced, those skilled in the art could make numerous alterations to the disclosed embodiments without departing from the scope of the present disclosure and the appended claims. It is intended that all matter contained in the above description or shown in the accompanying drawings shall be interpreted as illustrative only and not limiting. Accordingly, the examples and embodiments herein should not be construed as limiting the scope of the disclosure. Changes in detail or structure may be made without departing from the present teachings. The foregoing description and following claims are intended to cover all such modifications and variations.

Various embodiments are described herein of various apparatuses, systems, and methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements may not have been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

The terms "including," "comprising" and variations thereof, as used in this disclosure, mean "including, but not limited to," unless express specified otherwise. The terms "a," "an," and "the," as used in this disclosure, means "one or more," unless expressly specified otherwise.

Reference throughout the specification to "various embodiments," "some embodiments," "one embodiment," "an embodiment," or the like, means that a particular feature, structure, or characteristic described in connection with the embodiment is included in at least one embodiment. Thus, appearances of the phrases "in various embodiments," "in some embodiments," "in one embodiment," "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation.

Although process steps, method steps, algorithms, or the like, may be described in a sequential order, such processes, methods, and algorithms may be configured to work in alternative orders. In other words, any sequence or order of steps that may be described does not necessarily indicate a requirement that the steps be performed in that order. The steps of the processes, methods, and algorithms described herein may be performed in any order practical. Further, some steps may be performed simultaneously.

When a single device or article is described herein, it will be readily apparent that more than one device or article may be used in place of a single device or article. Similarly, where more than one device or article is described herein, it will be readily apparent that a single device or article may be used in place of the more than one device or article. The functionality or the features of a device may be alternatively embodied by one or more other devices which are not explicitly described as having such functionality or features.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. However, surgical instruments may be used in many orientations and positions, and these terms are not intended to be limiting and absolute. All other directional or spatial references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. An ablation balloon catheter apparatus comprising:
a catheter shaft including a proximal portion and a distal portion;
an ablation balloon including a proximal end and a distal end, the proximal end coupled to the distal portion of the catheter shaft, the ablation balloon comprising:
an uncoated region configured to facilitate energy transfer between the ablation balloon and tissue in contact with the uncoated region;
at least one coated region at the proximal end of the ablation balloon, the at least one coated region configured to mitigate energy transfer between the ablation balloon and tissue in contact with the at least one coated region; and
a border between the uncoated region and the at least one coated region; and
at least one electrode support structure extending substantially longitudinally across a surface of the ablation balloon; and
a corresponding flexible electronic circuit coupled to each at least one electrode support, each flexible electronic circuit respectively comprising:
at least one trace extending longitudinally across the ablation balloon; and
a diagnostic electrode positioned at least partly within the border between the coated region and the uncoated region.

2. The apparatus of claim 1, wherein the uncoated region of the ablation balloon is configured to engage a pulmonary vein and ablate tissue along a circumferential region around the pulmonary vein in contact with the uncoated region of the ablation balloon.

3. The apparatus of claim 1, wherein the uncoated region is situated at a distal end of the ablation balloon.

4. The apparatus of claim 1, further comprising:
a generator configured to generate electroporation pulses and transmit the electroporation pulses to the uncoated region to ablate tissue in contact with the uncoated region.

5. The apparatus of claim 4, wherein the at least one coated region of the ablation balloon is configured to shield tissue in contact with the at least one coated region from the electroporation pulses.

6. The apparatus of claim 1, wherein each diagnostic electrode is configured to detect electrophysiological characteristics of tissue in contact with the diagnostic electrode.

7. The apparatus of claim 1, wherein each at least one trace electrically couples the corresponding diagnostic electrode to a lead wire, and the diagnostic electrode is configured to measure potentials across ablated tissue.

8. An ablation balloon catheter apparatus comprising:
a catheter shaft including a proximal portion and a distal portion;
an ablation balloon including a proximal end and a distal end, the proximal end coupled to a distal portion of the catheter shaft, the ablation balloon comprising:
an uncoated region configured to facilitate energy transfer between the ablation balloon and tissue in contact with the uncoated region;
at least one coated region at the proximal end of the ablation balloon, the at least one coated region configured to mitigate energy transfer between the ablation balloon and tissue in contact with the at least one coated region; and
a border between the uncoated region and the at least one coated region; and
a flexible electronic circuit coupled to and extending across the coated region of the ablation balloon, the flexible electronic circuit comprising:
at least one trace extending longitudinally across a surface of the ablation balloon; and
a diagnostic electrode positioned at least partly within the border between the coated region and the uncoated region,
wherein the at least one trace is configured to electrically couple the diagnostic electrode to a lead wire, the diagnostic electrode configured to measure potentials across ablated tissue.

9. The apparatus of claim 8, wherein the uncoated region of the ablation balloon is configured to engage a pulmonary vein and ablate tissue along a circumferential region around the pulmonary vein in contact with the uncoated region of the ablation balloon.

10. The apparatus of claim 8, wherein the diagnostic electrode is circumferentially distributed about the flexible electronic circuit and is configured to conduct electrical signals indicative of tissue health in contact with the diagnostic electrode to controller circuitry at a proximal end of the catheter shaft.

11. The apparatus of claim 8, further including at least one support structure extending over the surface of the ablation balloon and supporting the flexible electronic circuit.

12. The apparatus of claim 11, wherein the at least one support structure comprises a spline on which the flexible electronic circuit is disposed; and
wherein the support structure comprises a plurality of legs, and wherein the diagnostic electrode is secured to one of the plurality of legs.

13. The apparatus of claim 11, wherein the at least one support structure comprises a spline on which the flexible electronic circuit is disposed, the flexible electronic circuit having plurality of electrode support structures, and wherein the diagnostic electrode is secured to one of the plurality of electrode support structure.

14. The apparatus of claim 8, wherein the uncoated region is positioned at the distal end of the ablation balloon.

15. The apparatus of claim 8, further comprising:
a generator configured to generate electroporation pulses and transmit the electroporation pulses to the uncoated region to ablate tissue in contact with the uncoated region as an ablation therapy.

16. The apparatus of claim 15, wherein the at least one coated region of the ablation balloon is configured to shield tissue in contact with the at least one coated region from the electroporation pulses.

17. The apparatus of claim 15, wherein the at least one coated region is configured to insulate a blood pool and pulmonary vein tissue in contact with the at least one coated region from the electroporation pulses.

18. The apparatus of claim 15, wherein the ablation therapy creates a circumferential zone of ablation around the tissue in contact with the uncoated region.

\* \* \* \* \*